US008336550B2

(12) United States Patent
Goldstein

(10) Patent No.: US 8,336,550 B2
(45) Date of Patent: Dec. 25, 2012

(54) RESPIRATORY DEVICE

(76) Inventor: Joseph Goldstein, Los Angeles, CA (US)

( * ) Notice: Subject to any disclaimer, the term of this patent is extended or adjusted under 35 U.S.C. 154(b) by 0 days.

(21) Appl. No.: 13/284,846

(22) Filed: Oct. 28, 2011

(65) Prior Publication Data

US 2012/0103343 A1 May 3, 2012

Related U.S. Application Data

(60) Provisional application No. 61/456,074, filed on Nov. 1, 2010, provisional application No. 61/456,077, filed on Nov. 1, 2010, provisional application No. 61/344,992, filed on Dec. 2, 2010, provisional application No. 61/459,209, filed on Dec. 9, 2010.

(51) Int. Cl.
*A62B 18/08* (2006.01)
*A62B 18/02* (2006.01)
*A62B 7/00* (2006.01)
*A61M 15/08* (2006.01)
*A61M 16/00* (2006.01)

(52) U.S. Cl. ......... 128/206.29; 128/200.24; 128/200.26; 128/206.21; 128/206.28; 128/207.14; 128/207.18

(58) Field of Classification Search .................. 128/848, 128/857, 859–861, 200.24, 200.26, 201.11, 128/201.26, 201.27, 203.22, 206.11, 206.12, 128/206.29, 207.14, 207.18; 405/185–187
See application file for complete search history.

(56) References Cited

U.S. PATENT DOCUMENTS

| 4,967,744 | A | | 11/1990 | Chua | |
|---|---|---|---|---|---|
| 5,537,994 | A | | 7/1996 | Thornton | |
| 5,752,510 | A | | 5/1998 | Goldstein | |
| 5,954,048 | A | * | 9/1999 | Thornton | 128/201.18 |
| 5,983,892 | A | | 11/1999 | Thornton | |
| 6,012,455 | A | | 1/2000 | Goldstein | |
| 6,209,542 | B1 | | 4/2001 | Thornton | |
| 6,374,824 | B1 | * | 4/2002 | Thornton | 128/201.26 |
| 6,789,543 | B2 | * | 9/2004 | Cannon | 128/207.18 |
| 7,021,312 | B2 | * | 4/2006 | Cannon | 128/206.29 |
| 7,195,018 | B1 | * | 3/2007 | Goldstein | 128/207.18 |
| 2008/0149105 | A1 | | 6/2008 | Matula et al. | |
| 2008/0276938 | A1 | * | 11/2008 | Jeppesen et al. | 128/204.18 |
| 2011/0155140 | A1 | * | 6/2011 | Ho et al. | 128/207.18 |

* cited by examiner

*Primary Examiner* — Annette Dixon
(74) *Attorney, Agent, or Firm* — Crandall Patent Group LLC; Jerry A. Crandall Esq.

(57) ABSTRACT

In an embodiment, a respiratory device is disclosed. The respiratory device may include a nasal device. The respiratory device may also include a conveyor device coupled with the nasal device. The respiratory device may further include an oral device, wherein the oral device may include an adjustment nut sized to couple with the conveyor device.

20 Claims, 10 Drawing Sheets

RESPIRATORY DEVICE

CROSS REFERENCE TO RELATED APPLICATIONS

This application claims the benefit of U.S. Provisional Application No. 61/456,074, filed on Nov. 1, 2010, U.S. Provisional Application No. 61/456,077, filed on Nov. 1, 2010, U.S. Provisional Application No. 61/344,992, filed on Dec. 2, 2010, and U.S. Provisional Application No. 61/459,209, filed on Dec. 9, 2010, which is each incorporated herein by reference in its entirety.

TECHNICAL FIELD

The present application relates to the field of respiratory devices.

BACKGROUND

Respiration may be defined as the transportation of specific gases between the ambient air and an individual's lungs. For a multitude of respiratory ailments, such as, but not limited to, snoring and sleep apnea, various ventilation techniques may be implemented to aid with inhalation and exhalation during the respiration process.

SUMMARY

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter.

In an embodiment, a respiratory device is disclosed. The respiratory device may include or comprise a nasal device. The respiratory device may also include or comprise a conveyor device coupled with the nasal device. The respiratory device may further include or comprise an oral device, wherein the oral device may include or comprise an adjustment nut sized to couple with the conveyor device.

Additionally, in one embodiment, a respiratory device is disclosed, wherein the respiratory device may include or comprise a nasal device. The respiratory device may also include or comprise a conveyor device coupled with the nasal device, wherein the conveyor device may include or comprise a first surface that defines a first spiral thread. The respiratory device may further include or comprise an oral device coupled with the conveyor device, wherein the oral device may include or comprise an adjustment nut. The adjustment nut may include or comprise a second surface that defines a second spiral thread sized to engage the first spiral thread.

Moreover, in an embodiment, a respiratory device is disclosed, wherein the respiratory device may include or comprise a nasal device. The respiratory device may also include or comprise a conveyor device coupled with the nasal device, wherein first and second openings are respectively defined at opposite ends of the conveyor device. The respiratory device may further include or comprise an oral device coupled with the conveyor device, wherein the oral device is sized to rotate around the conveyor device so as to be repositioned toward one of the first and second openings and away from the other of the first and second openings.

DESCRIPTION OF THE DRAWINGS

The accompanying drawings, which are incorporated in and form a part of this specification, illustrate embodiments of the present technology, and, together with the Detailed Description, serve to explain principles discussed below.

Figure 1:
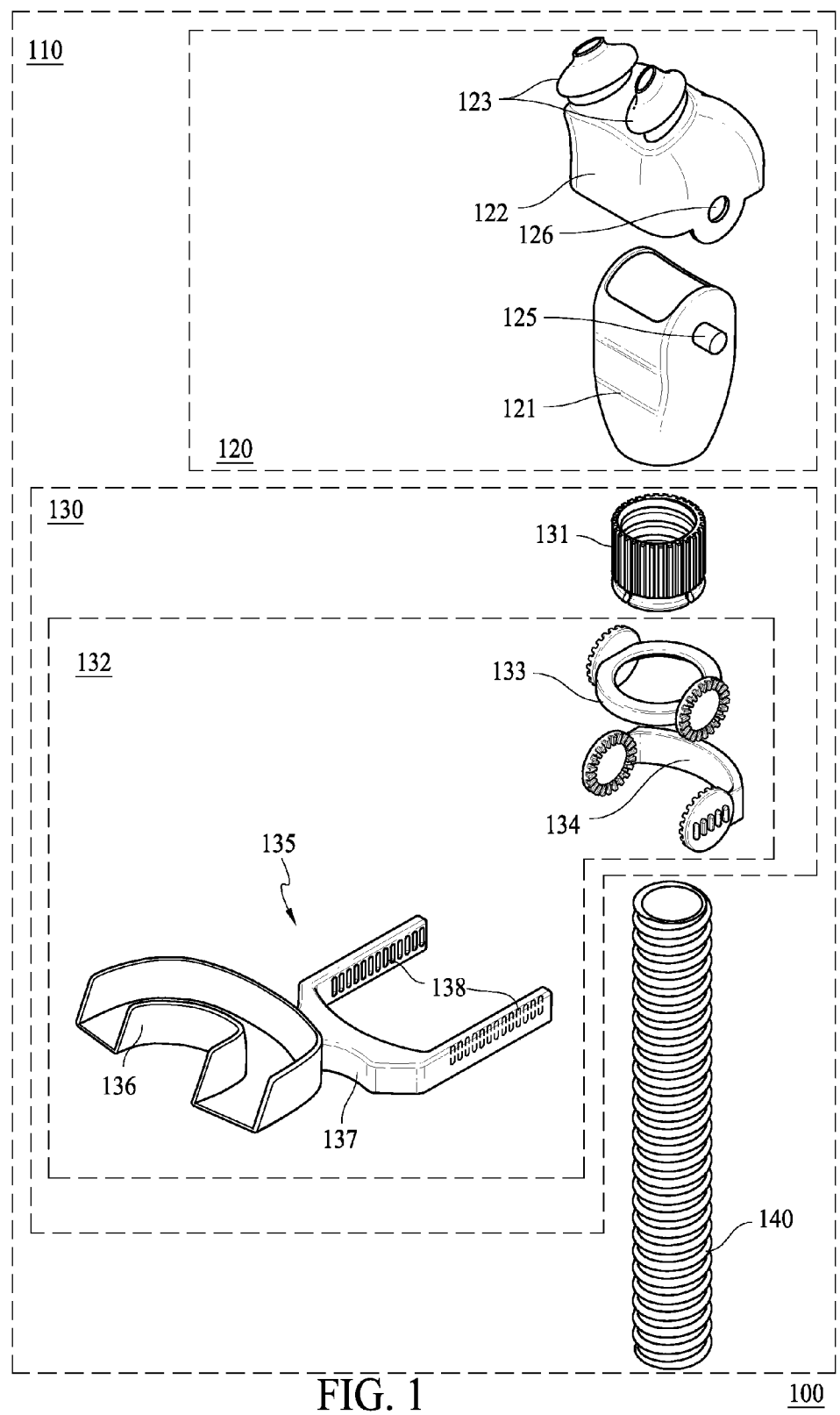
FIG. 1 is an exploded view of a first exemplary respiratory device in accordance with an embodiment.

The drawings referred to in this description are not to be understood as being drawn to scale except if specifically noted, and such drawings are only exemplary in nature.

DETAILED DESCRIPTION

Reference will now be made in detail to embodiments of the present technology, examples of which are illustrated in the accompanying drawings. While the present technology will be described in conjunction with various embodiments, these embodiments are not intended to limit the present technology. Rather, the present technology is to be understood as encompassing various alternatives, modifications and equivalents.

Moreover, in the following Detailed Description, numerous specific details are set forth in order to provide a thorough understanding of the present technology. However, the present technology may be practiced without these specific details. In other instances, well-known methods, procedures, components, and circuits have not been described in detail so as to not unnecessarily obscure aspects of the exemplary embodiments presented herein.

Furthermore, the term "air" as used herein may be defined as referring to any gaseous substance, which may or may not be a mixture of different types of gases. Additionally, when two or more specified devices, apparatuses, components, etc., are herein described as being "coupled with" one another, it is noted that those specified devices, apparatuses, components, etc., are not necessarily attached directly to one another; rather, one or more other devices, apparatuses, components, etc., may be coupled between the two or more specified devices, apparatuses, components, etc.

OVERVIEW

Various embodiments of the present technology pertain to respiratory treatments involving the introduction of various gases into a patient's airway, such as by applying a prescribed or preselected degree of gaseous air pressure into a patient's nostrils. For example, in an embodiment, a nasal interface is disclosed, wherein the nasal interface may be utilized, for example, for the treatment of sleep apnea, wherein air is blown into a patient's nostrils, as well as for a multitude of other ailments. This nasal interface may include, or be implemented with, for example, a positive air pressure (PAP) interface (e.g., a continuous positive air pressure (CPAP) interface, a variable positive air pressure (VPAP) interface, a bi-level positive air pressure (BIPAP) interface, and automatic positive air pressure (APAP) interface).

To illustrate, one embodiment provides a nasal interface having a nasal intake member that is coupled with or attached to the top outlet of a respiratory tube. Various gases are pumped under pressure, such as by a gas or air supply unit, through the respiratory tube and into the nasal intake member of the nasal interface, wherein the nasal intake member is configured to direct these gases into a patient's nostrils. Indeed, the nasal intake member may include, for example, a nasal plug component, wherein the nasal plug component includes a resilient component having two nasal plugs sized to be inserted into the patient's nostrils.

The foregoing notwithstanding, in one embodiment, the nasal interface is configured to be more comfortable, more lightweight and simpler to manufacture than various other exemplary respiratory devices. Indeed, in accordance with an embodiment, uncomfortable straps or headgear, which can irritate the patient, may be avoided, because a dental appliance or mouthpiece is implemented that can be affixed to or anchored with the patient's upper or lower teeth, or to both of the patient's upper and lower arches. In particular, the dental appliance or mouthpiece is anchored with a patient's jaw, and a bracket that extends outward from the dental appliance or mouthpiece protrudes out of the patient's mouth. Moreover, a hole is defined within the bracket such that a resilient respiratory tube may pass through a portion of the bracket positioned outside of the patient's mouth such that the tube extends upward toward the patient's nostrils.

Furthermore, in an embodiment, a nasal air intake device with multiple adjustments is disclosed. It includes a single inlet tube integrated with a mechanism configured to provide a variety of adjustments for maximum patient comfort. This single tube device may have one or several forward/backward pivot actions, an upward/downward actuator, and a stationary forward/backward slide adjustment configured to increase patient comfort. For example, an upper/downward nut/screw configuration may be implemented such that a position of the respiratory tube may be adjusted. In this manner, a proper fit and seal against the patient's nostrils may be achieved. Additionally, other adjustment features may also be implemented to further increase patient comfort.

To further illustrate, one embodiment provides that a dental appliance or mouthpiece is implemented, wherein an adjustment bracket extends outward from the dental appliance, and wherein a hole is defined within the adjustment bracket such that a resilient respiratory tube may pass through the adjustment bracket and extend upward toward the patient's nostrils. The adjustment bracket is shaped or configured such that the relative position of the tube can be adjusted in multiple different directions along a number of relative degrees of freedom. In this manner, the nasal intake member can be moved along the respiratory tube so as to increase patient comfort and treatment efficiency through a series of mechanical adjustments.

In view of the foregoing, it is noted that various embodiments of the present technology involve devices, which may include nasal interfaces and dental devices, and which may be utilized for the treatment of sleep apnea as well as for a multitude of other ailments. It is further noted, however, that the present technology is not limited to treatments solely within the sleep apnea regimen.

Various exemplary embodiments of the present technology will now be discussed. It is noted, however, that the present technology is not limited to these exemplary embodiments, and that the present technology also includes obvious variations of the exemplary embodiments and implementations described herein. It is further noted that various well-known components are generally not illustrated in the drawings so as to not unnecessarily obscure various principles discussed herein, but that such well-known components may be implemented by those skilled in the art to practice various embodiments of the present technology.

Exemplary Devices, Arrangements and Configurations

Various exemplary devices, arrangements and configurations for implementing various embodiments of the present technology will now be described. However, the present technology is not limited to these exemplary devices, arrangements and configurations. Indeed, other devices, arrangements and configurations may also be implemented.

With reference now to FIG. 1, an exploded view 100 of a first exemplary respiratory device 110 in accordance with an embodiment is shown. In particular, first exemplary respiratory device 110 includes a nasal device 120 (or nasal assembly). In an embodiment, nasal device 120, or a component thereof, is sized to direct an amount of air into a user's nasal cavity, such as to aid the user's respiration.

Although nasal device 120 is described herein with respect to various exemplary components and configurations, it is noted that the present technology is not limited to any particular type of nasal device. Indeed, in accordance with one embodiment, nasal device 120 includes a face mask, or a similar device, sized to fit on a facial region around a user's nose so as to direct an amount of air into a user's nasal cavity. This face mask may even include a sealing member (not shown) configured to prevent an escape of gases between nasal device 120 and the user's skin, and a head strap may be implemented to hold the face mask against the user's face.

With reference still to FIG. 1, it is noted that nasal device 120 may optionally include one or more of a primary support member 121, a secondary support member 122 and a number of nasal air intake members 123. Moreover, one or more of these components may have a hollow body such that air may pass through the respective components of nasal device 120. Furthermore, a number of nasal air intake members 123 may be sized to fit within a user's nostril.

To illustrate, one embodiment provides that nasal device 120 includes primary and secondary support members 121, 122. Additionally, a number of nasal air intake members 123 extend from secondary support member 122. In accordance with an exemplary implementation, air is routed through primary support member 121, and then through secondary support member 122, and then through a number of nasal air intake members 123, wherein each of nasal air intake members 123 are sized to fit within a user's nostril such that air may be directed through a number of nasal air intake members 123 and into the user's nasal cavity.

Furthermore, it is noted that nasal device 120 may be physically adjustable such that a position of a number of nasal air intake members 123 may be adjusted relative to a position of a user's nasal cavity. For example, one support member from among primary and secondary support members 121, 122 may include first and second protrusions, such as first exemplary protrusion 125, and the other support member from among the primary and secondary support members 121, 122 may include first and second receptacles, such as first exemplary receptacle 126, defined therein. The first and second protrusions are sized to fit within the first and second receptacles, respectively, such that primary and secondary support members 121, 122 are capable of supporting one another, and such that secondary support member 122 is capable of rotating relative to primary support member 121, or vice versa, such as further discussed herein.

The foregoing notwithstanding, in an embodiment, primary support member 121, a secondary support member 122 and a number of nasal air intake members 123 include a plastic bottom housing, a plastic top housing, and a silicon nose piece, respectively. It is noted, however, that the present technology is not limited to the use of any specific materials, and that materials other than plastic and silicon may be implemented.

With reference still to FIG. 1, first exemplary respiratory device 110 also includes an oral device 130, wherein oral device 130 may optionally include an adjustment member (or height adjustment ring), such as an adjustment nut 131. It is noted that the adjustment member may be configured to change a position of oral device 130 relative to nasal device 120 and/or relative to an air conveyance device, such as will be discussed herein. Additionally, oral device 130 may optionally include an oral assembly 132. In one embodiment, oral assembly 132 is fixedly coupled with, or extends from, the adjustment member such that oral assembly 132 is configured to resist a degree of movement relative to the adjustment member. Alternatively, oral assembly 132 may be configured to move relative to the adjustment member, such as will be further discussed herein.

Additionally, it is noted that oral assembly 132 may optionally include one or more of a first support member 133, a second support member 134 and an oral member 135. It is further noted that oral member 135 may optionally include one or more of a dental anchor 136 (which may be sized to anchor to a dental region of a user), a primary extension 137 (which may extend from dental anchor 136), and first and second secondary extensions 138 (which may extend from dental anchor 136 or primary extension 137). In accordance with one embodiment, oral device 130 is configured to anchor first exemplary respiratory device 110 when first exemplary respiratory device 110 is to be used, such as when dental anchor 136 (which may be referred to as a dental appliance or mouthpiece) is anchored to a dental region of a user.

The foregoing notwithstanding, although oral device 130 is described herein with respect to various exemplary components and configurations, it is noted that the present technology is not limited to any particular type of oral device. For example, in accordance with one embodiment, oral device 130 includes dental anchor 136, wherein dental anchor 136 is sized to anchor to a user's upper and/or lower dental region. Alternatively, a different type of oral device may be implemented.

With reference still to FIG. 1, first exemplary respiratory device 110 further includes a conveyor device 140, wherein conveyor device 140 is sized to direct an amount of gas toward nasal device 120. Consider the example where conveyor device 140 is a tube having a hollowed body with openings at opposite ends thereof. Nasal device 120 is coupled with or attached to an end of this tube such that air may be pumped through the tube, such as with a gas or air supply unit (which may include an air compressor), and into nasal device 120. Nasal device 120 then may be implemented to direct the air into a user's nasal cavity, such as to aid the user's respiration.

The foregoing notwithstanding, although conveyor device 140 is described herein with respect to various exemplary geometric configurations, it is noted that the present technology is not limited to any particular type of conveyor device. For example, in accordance with one embodiment, conveyor device 140 is a rubber or plastic hose. Alternatively, a different type of conveyor device may be implemented.

Figure 2A:
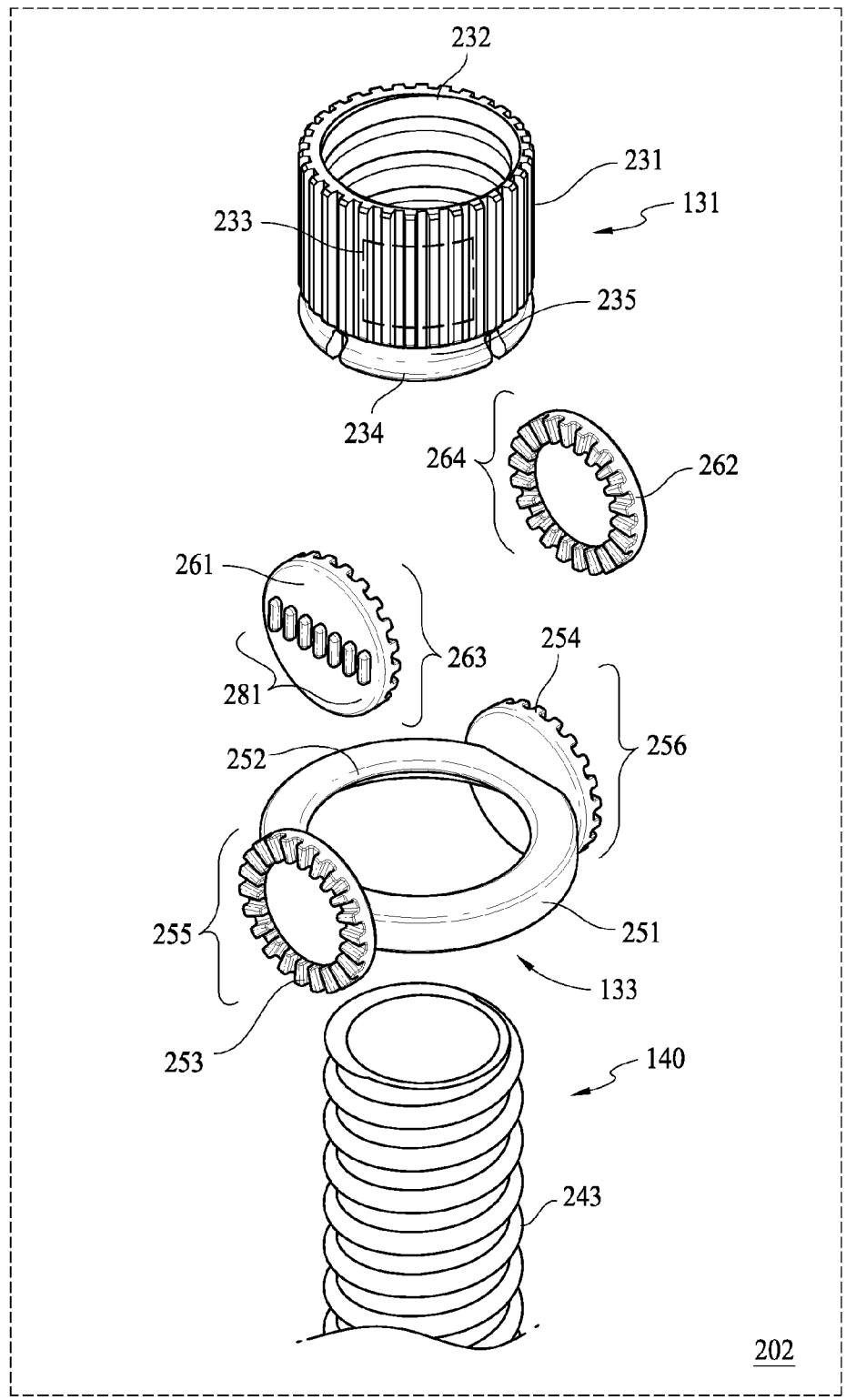
FIG. 2A is an exploded view of a number of components of an exemplary respiratory device in accordance with an embodiment.
Figure 2B:
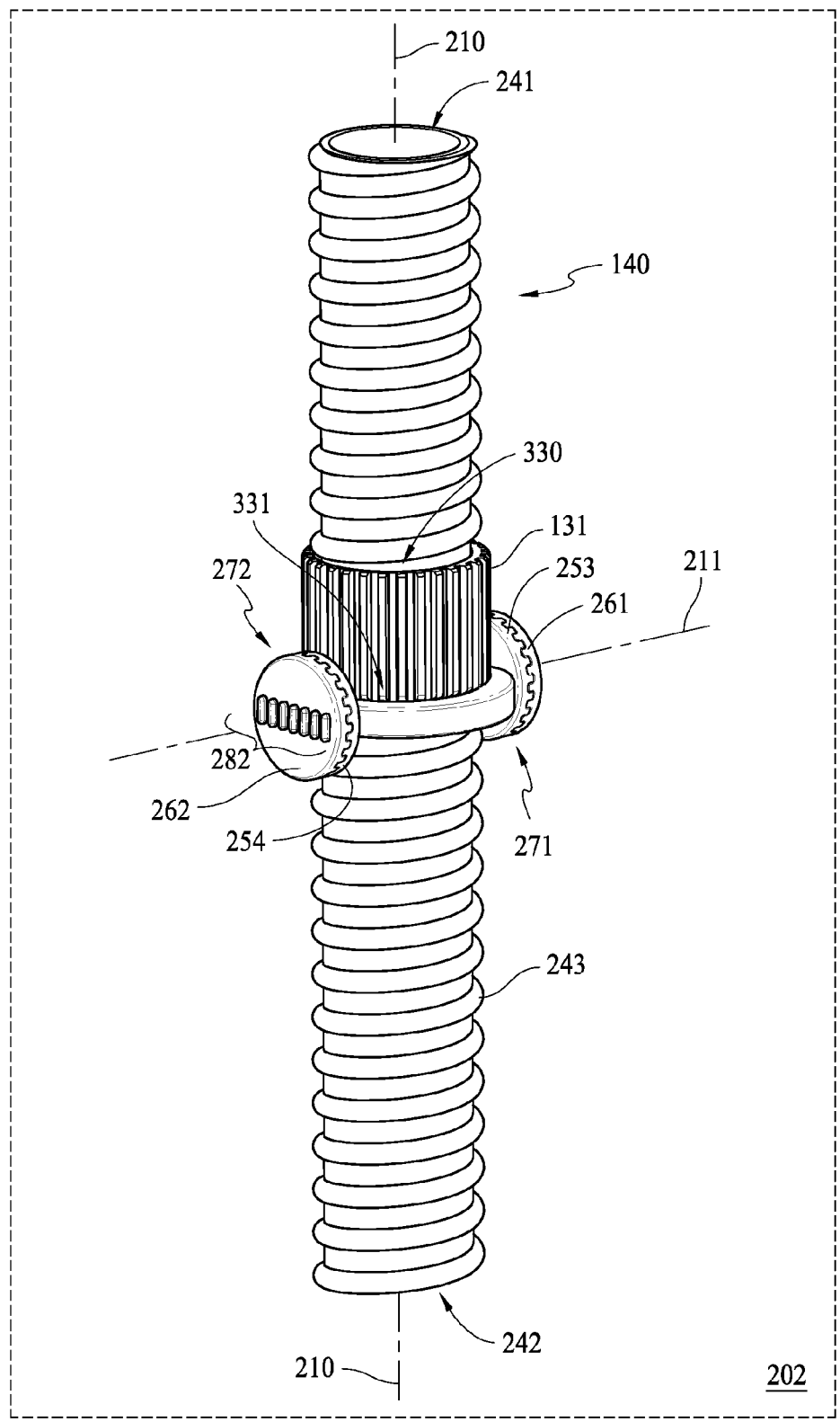
FIG. 2B is an assembled view of a number of components of an exemplary respiratory device in accordance with an embodiment.

With reference now to FIGS. 2A and 2B, exploded and assembled views 200, 201, respectively, of a number of components 202 of an exemplary respiratory device, such as first exemplary respiratory device 110, in accordance with an embodiment are shown. Components 202 include conveyor device 140, wherein first and second openings 241, 242 are defined at opposite ends of conveyor device 140. Components 202 also include adjustment nut 131, wherein adjustment nut 131 is sized to be coupled with or mounted on conveyor device 140.

In particular, an embodiment provides that conveyor device 140 has or includes an outer surface that defines a first geometric thread, such as first spiral thread 243 illustrated in FIGS. 2A and 2B. Additionally, adjustment nut 131 includes a first base member 231 that has or includes an inner surface that defines a second geometric thread, such as second spiral thread 232 illustrated in FIGS. 2A and 2B. These two geometric threads are sized to engage one another such that adjustment nut 131 may be coupled with or mounted on conveyor device 140, and such that adjustment nut 131 may be rotated relative to conveyor device 140, or vice versa, to thereby reposition adjustment nut 131 along a length of conveyor device 140.

To further illustrate, consider the example where conveyor device 140 has or includes an outer surface that defines first spiral thread 243, and wherein first base member 231 of adjustment nut 131 has or includes an inner surface that defines second spiral thread 232. Second spiral thread 232 is sized to engage or fit within the first spiral thread 243 of conveyor device 140, because the geometries of first and second spiral threads 243, 232 complement one another. In this manner, adjustment nut 131 may be screwed onto conveyor device 140, such as around a first axis of rotation 210, or conveyor device 140 may be screwed into adjustment nut 131, such that adjustment nut 131 is coupled with or mounted on conveyor device 140, and such that a screw joint 330 is defined between adjustment nut 131 and conveyor device 140.

Furthermore, pursuant to one embodiment, once mounted on conveyor device 140, adjustment nut 131 may be rotated relative to conveyor device 140, or vice versa, such that adjustment nut 131 is repositioned toward one of first and second openings 241, 242, and consequently away from the other of first and second openings 241, 242. Moreover, first base member 231 may have an outer surface that defines a number of serrations or grips, such as exemplary serrations or grips 233, so as to enable a user to more easily turn adjustment nut 131 relative to conveyor device 140.

With reference still to FIGS. 2A and 2B, adjustment nut 131 also includes one or more physical lips, such as physical lip 234, coupled with or extending from first base member 231 such that a receptacle 235 is defined between an edge of first base member 231 and physical lip 234. Additionally, components 202 further include first support member 133, which may be referred to as a hose ring. First support member 133 has or includes a second base member 251, wherein a protrusion 252 (which may be extending inwards) is coupled with or extends from second base member 251 and is sized to engage (e.g., fit inside) receptacle 235 such that (1) physical lip 234 is capable of supporting first support member 133 relative to adjustment nut 131, (2) protrusion 252 is capable of supporting adjustment nut 131 relative to first support member 133, and (3) a first revolute joint 331 is defined between adjustment nut 131 and first support member 133.

In an embodiment, first support member 133 further includes first and second coupling members 253, 254 coupled with or extending from second base member 251, wherein first and second coupling members 253, 254 include first and second sets of physical teeth 255, 256, respectively. Additionally, components 202 include third and fourth coupling members 261, 262, wherein third and fourth coupling members 261, 262 include third and fourth sets of physical teeth 263, 264, respectively. It is noted that first and third sets of physical teeth 255, 263 are each sized to engage, or interlock with, one another in a first relative tooth arrangement 271, and that second and fourth sets of physical teeth 256, 264 are each sized to engage, or interlock with, one another in a second relative tooth arrangement 272 (see, e.g., FIG. 2B).

As will be further described herein, an embodiment provides that the interlocked sets of physical teeth prevent a rotation of first and second support members 133, 134 relative to one another until a preselected degree of physical force is applied to one of first and second support members 133, 134, at which point (1) first and third sets of physical teeth 255, 263 will consequently rotate relative to one another and then engage, or interlock with, one another in a third relative tooth arrangement, and (2) second and fourth sets of physical teeth 256, 264 will consequently rotate relative to one another and then engage, or interlock with, one another in a fourth relative tooth arrangement.

Thus, in accordance with an embodiment, third and fourth coupling members 261, 262 are portions of second support member 134 (not shown), and the aforementioned teeth engage one another as described such that first and second support members 133, 134 are capable of supporting one another when in a first relative position associated with first and second relative tooth arrangements 271, 272. Additionally, a rotation of first coupling member 253 relative to third coupling member 261 and of second coupling member 254 relative to fourth coupling member 262 (or vice versa), along a second axis of rotation 211 causes first and third sets of physical teeth 255, 263 to engage one another in a third relative tooth arrangement, and second and fourth sets of physical teeth 256, 264 to engage one another in a fourth relative tooth arrangement, such that first and second support members 133, 134 are capable of supporting one another when in a second relative position associated with the third and fourth relative tooth arrangements.

Furthermore, in an embodiment, first and second secondary extensions 138 of oral member 135 include first and second groups of physical teeth (not shown), respectively. Moreover, and with reference still to FIGS. 2A and 2B, third and fourth coupling members 261, 262 include third and fourth groups of physical teeth 281, 282, respectively. The first and second groups of physical teeth of first and second secondary extensions 138 are sized to engage or interlock with third and fourth groups of physical teeth 281, 282 such that oral member 135 is supported relative to second support member 134 (not shown), or vice versa, as will be further discussed herein.

Figure 3:
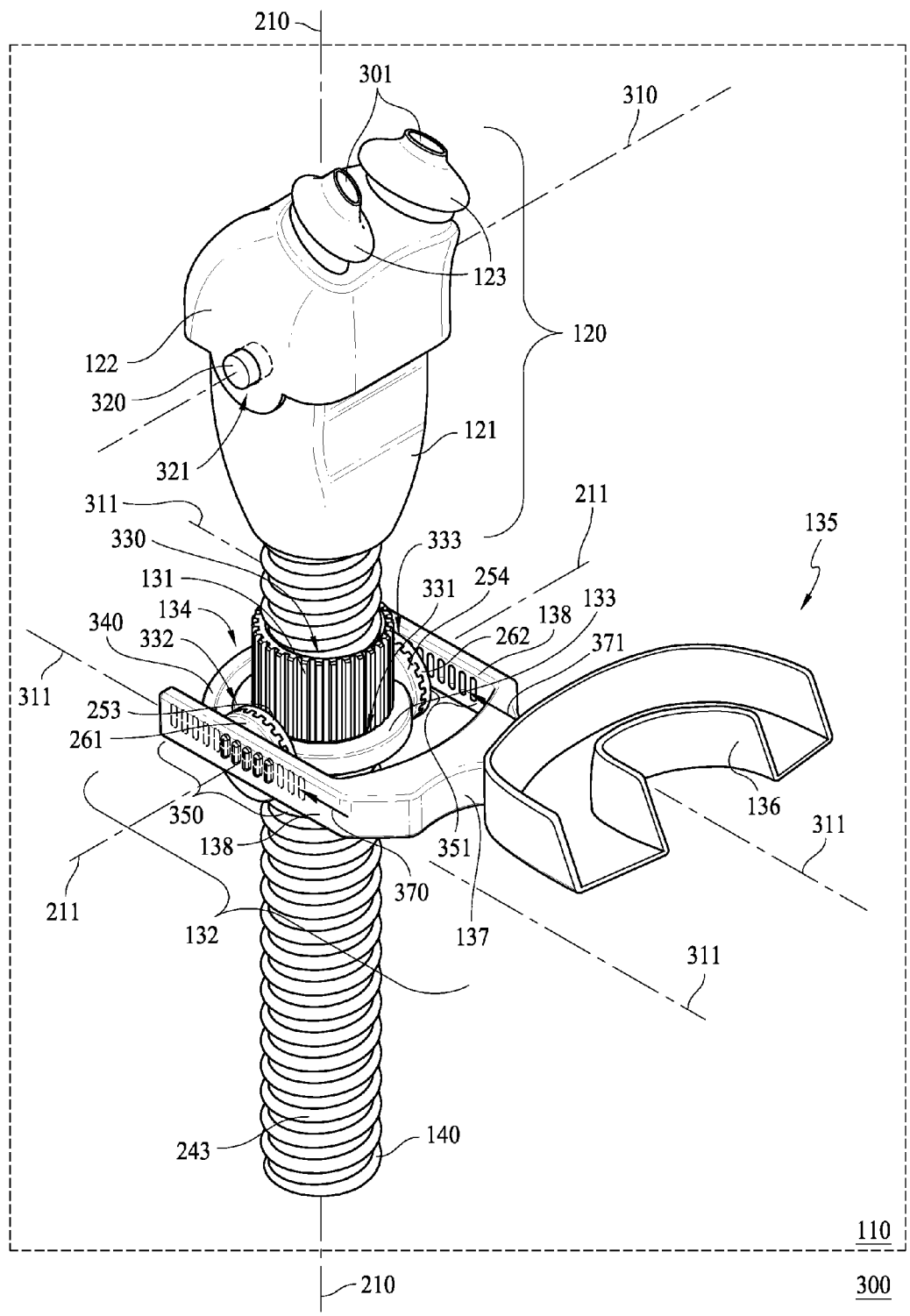
FIG. 3 is an assembled view of a first exemplary respiratory device in accordance with an embodiment.

With reference now to FIG. 3, an assembled view 300 of first exemplary respiratory device 110 in accordance with an embodiment is shown. First exemplary respiratory device 110 includes nasal device 120 and conveyor device 140, wherein nasal device 120 is coupled with or attached to an end of conveyor device 140. Pursuant to an exemplary implementation, first and second openings 241, 242 are respectively defined at opposite ends of conveyor device 140 (see FIG. 2B) such that conveyor device 140 may be used to direct a substance (e.g., a gas) into nasal device 120.

For purposes of illustration, an embodiment provides that conveyor device 140 includes a device or component, such as a hose, positioned to convey a substance, such as oxygenated air, into nasal device 120. Nasal device 120 may then be used to direct the substance into a user's nasal cavity. Indeed, in one embodiment, nasal device 120 includes a number of nasal air intake members 123 sized to direct an amount of air into a user's nasal cavity, such as to aid the user's respiration.

With reference still to FIG. 3, and in accordance with an embodiment, nasal device 120 includes primary support member 121 and secondary support member 122, wherein primary support member 121 is coupled with or attached to an end of conveyor device 140. It is noted that conveyor device 140 may include a device or component, such as a hose, positioned to convey a substance, such as oxygenated air, into primary support member 121, which is then conveyed into secondary support member 122, and, consequently, into a number of nasal air intake members 123. A number of nasal air intake members 123 may then be used to direct the substance into a user's nasal cavity, such as through a number of openings 301 defined in nasal air intake members 123.

Moreover, pursuant to one embodiment, secondary support member 122 is moveably coupled with primary support member 121 such as to be rotatable relative to primary support member 121 around a third axis of rotation 310. In this manner, a position of, for example, a number of nasal air intake members 123 relative to primary support member 121 may be adjusted, such as to increase a degree of comfort associated with nasal device 120. Furthermore, an embodiment provides that nasal air intake members 123 are configured to be flexible during an operation of first exemplary respiratory device 110, such as to further increase a degree of comfort associated with nasal device 120, and particularly with nasal air intake members 123.

Furthermore, in accordance with an embodiment, one support member from among primary and secondary support members 121, 122 includes first and second protrusions; such as second exemplary protrusion 320, positioned along third axis of rotation 310, and the other support member from among the primary and secondary support members 121, 122 includes first and second receptacles, such as second exemplary receptacle 321, defined therein along third axis of rotation 310. The first and second receptacles are sized to receive the first and second protrusions, respectively, such that primary and secondary support members 121, 122 are capable of supporting one another, and such that primary and secondary support members 121, 122 are capable of rotating relative to one another about third axis of rotation 310. In particular, the first and second protrusions are sized to fit within the first and second receptacles, respectively, to thereby define or create primary and secondary revolute joints along third axis of rotation 310. Thus, it is noted that, pursuant to one embodiment, nasal device 120 may be physically adjustable such that a position of a number of nasal air intake members 123 may be adjusted relative to a position of a user's nasal cavity.

With reference still to FIG. 3, and with reference again to FIG. 1, an embodiment provides that first exemplary respiratory device 110 includes oral device 130 of FIG. 1, wherein oral device 130 is coupled with or mounted on conveyor device 140. Moreover, oral device 130 is sized to rotate around conveyor device 140, such as about screw joint 330, so as to be repositioned toward one of first and second openings 241, 242 (see FIG. 2B) of conveyor device 140 and away from the other of first and second openings 241, 242.

As previously stated, is noted that the present technology is not limited to any particular type of oral device. In one embodiment, however, oral device 130 includes adjustment nut 131, which is moveably coupled with or mounted on conveyor device 140 such that adjustment nut 131 is capable of rotating relative to conveyor device 140 around first axis of rotation 210, and vice versa.

Consider the example where conveyor device 140 has an outer surface that defines first spiral thread 243, and wherein adjustment nut 131 has an inner surface that defines second spiral thread 232 (see FIG. 2A) sized to engage or fit within first spiral thread 243. Rotating adjustment nut 131 relative to conveyor device 140 about screw joint 330 causes adjustment nut 131 to travel along the outer surface of conveyor device 140. In particular, in so much as first and second openings 241, 242 are respectively defined at opposite ends of conveyor device 140 (see FIG. 2B), adjustment nut 131 is sized to rotate around conveyor device 140 so as to reposition oral device 130 toward one of first and second openings 241, 242 and away from the other of first and second openings 241, 242. Moreover, in an embodiment, oral device 130 includes oral assembly 132 of FIG. 1, wherein oral assembly 132 is coupled with adjustment nut 131 such that oral assembly 132 is also capable of rotating relative to conveyor device 140 around first axis of rotation 210, and vice versa.

In one embodiment, oral assembly 132 is moveably coupled with adjustment nut 131 such that oral assembly 132 is capable of rotating relative to adjustment nut 131 around first axis of rotation 210. To illustrate, and with reference still to FIG. 3, consider the example where oral assembly 132 includes first support member 133, which is moveably coupled with adjustment nut 131 about first revolute joint 331. Adjustment nut 131 and first support member 133 are configured to rotate relative to one another about first revolute joint 331 and around first axis of rotation 210.

Alternatively, or in addition to the foregoing, an embodiment provides that oral assembly 132 includes first and second support members 133, 134, wherein second support member 134 is moveably coupled with first support member 133 about second and third revolute joints 332, 333. First and second support members 133, 134 are configured to rotate relative to one another about second and third revolute joints 332, 333 and around second axis of rotation 211.

To further illustrate, and with reference again to FIGS. 2A and 2B, an embodiment provides that first support member 133 includes second base member 251 as well as first and second coupling members 253, 254 coupled with or extending from second base member 251, wherein first and second coupling members 253, 254 include first and second sets of physical teeth 255, 256, respectively. Additionally, second support member 134 includes a third base member 340, as well as third and fourth coupling members 261, 262, which are coupled with or extending from third base member 340, wherein third and fourth coupling members 261, 262 include third and fourth sets of physical teeth 263, 264, respectively. First and third sets of physical teeth 255, 263 are each sized to engage, or interlock with, one another in a first relative tooth arrangement 271, and second and fourth sets of physical teeth 256, 264 are each sized to engage one another in a second relative tooth arrangement 272.

In an embodiment, these teeth engage one another as described above such that first and second support members 133, 134 are capable of supporting one another when in a first relative position associated with the first and second relative tooth arrangements. Additionally, a rotation of first coupling member 253 relative to third coupling member 261, and of second coupling member 254 relative to fourth coupling member 262 (or vice versa), along second axis of rotation 211 causes first and third sets of physical teeth 255, 263 to engage or interlock with one another in a third relative tooth arrangement, and second and fourth sets of physical teeth 256, 264 to engage or interlock with one another in a fourth relative tooth arrangement, such that first and second support members 133, 134 are capable of supporting one another when in a second relative position associated with the third and fourth relative tooth arrangements.

Thus, an embodiment provides that the interlocked sets of physical teeth prevent a rotation of first and second support members 133, 134 relative to one another until a preselected degree of physical force is applied to one of first and second support members 133, 134, at which point (1) first and third sets of physical teeth 255, 263 will consequently rotate relative to one another and then reengage, or interlock with, one another in a third relative tooth arrangement, and (2) second and fourth sets of physical teeth 256, 264 will consequently rotate relative to one another and then reengage, or interlock with, one another in a fourth relative tooth arrangement.

With reference still to FIG. 3, in an embodiment, oral assembly 132 includes oral member 135, wherein oral member 135 optionally includes dental anchor 136, which may be configured to anchor oral member 135 to a user's upper and/or lower dental regions such that first exemplary respiratory device 110 is supported relative to the user during an operation of first exemplary respiratory device 110. Moreover, in one embodiment, oral member 135 is moveably coupled with second support member 134 such that oral member 135 is capable of linearly sliding along one or more linear axes 311 relative to second support member 134, and vice versa. To illustrate, consider the example where oral assembly 132 also includes primary extension 137, which is coupled with or extending from dental anchor 136, as well as first and second secondary extensions 138, which are coupled with or extending from primary extension 137. First and second secondary extensions 138 are moveably coupled with second support member 134 and configured to linearly slide relative to second support member 134 along first and second sliding joints 370, 371, respectively, as well as respectively along linear axes 311.

Furthermore, in an embodiment, first and second secondary extensions 138 of oral member 135 include first and second groups of physical teeth 350, 351, respectively. It is noted that these teeth, as well as a number of physical indentations associated therewith, may be molded into first and second secondary extensions 138 through, for example, an injection molding process. Moreover, and with reference still to FIGS. 2A and 2B, third and fourth coupling members 261, 262 include third and fourth groups of physical teeth 281, 282, respectively. The groups of physical teeth of first and second secondary extensions 138 are sized to engage or interlock with third and fourth groups of physical teeth 281, 282, respectively, such that second support member 134 and oral member 135 are capable of supporting one another.

To further illustrate, and in accordance with an exemplary implementation, first and third groups of physical teeth 350, 281 are each sized to engage or interlock with one another in a fifth relative tooth arrangement, and second and fourth groups of physical teeth 351, 282 are each sized to engage one another in a sixth relative tooth arrangement, such that first and second secondary extensions 138 are capable of supporting second support member 134 when first and second secondary extensions 138 and second support member 134 are in a third relative position associated with the fifth and sixth relative tooth arrangements (as shown, for example, in FIG. 3). Moreover, a linear movement of one of first and second secondary extensions 138 relative to third coupling member 261 along first sliding joint 370, and of the other of first and second secondary extensions 138 relative to fourth coupling member 262 along second sliding joint 371, causes first and third groups of physical teeth 350, 281 to reengage or interlock with one another in a seventh relative tooth arrangement, and the second and fourth groups of physical teeth 351, 282 to reengage or interlock with one another in an eighth relative tooth arrangement, such that first and second secondary extensions 138 are capable of supporting second support member 134 when first and second secondary extensions 138 and second support member 134 are in a fourth relative position associated with the seventh and eighth relative tooth arrangements.

Thus, an embodiment provides that the interlocked sets of physical teeth prevent a linear movement of second support member 134 and oral member 135 relative to one another until a preselected degree of physical force is applied to one of second support member 134 and oral member 135, at which point (1) first and third groups of physical teeth 350, 281 will consequently slide relative to one another and then reengage, or interlock with, one another in a seventh relative tooth arrangement, and (2) second and fourth groups of physical teeth 351, 282 will consequently slide relative to one another and then reengage, or interlock with, one another in an eighth relative tooth arrangement.

In view of the foregoing, it is noted that various embodiments of the present technology are directed to a respiratory device that include one or more devices, apparatuses, components, etc. In an embodiment, one or more of these devices, apparatuses, components, etc., may be fabricated, such as through an injection molding process, so as to include, for example, a plastic or silicon material. It is noted, however, that the present technology is not limited to the use of any specific materials, and that materials other than plastic and silicon may be implemented.

Exemplary Adjustment Configurations

Figure 4A:
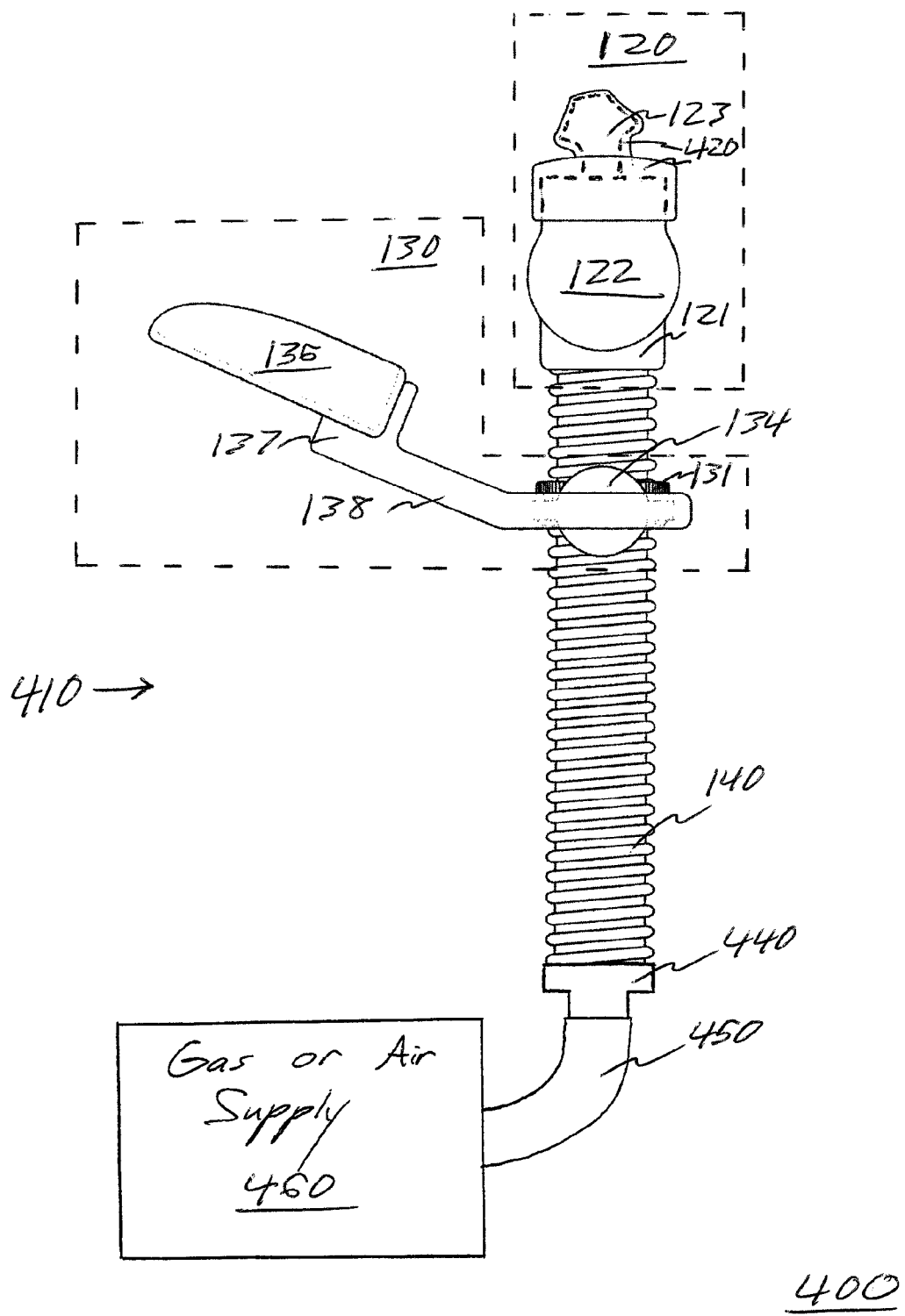
FIG. 4A is a side view of a second exemplary respiratory device in accordance with an embodiment.
Figure 4B:
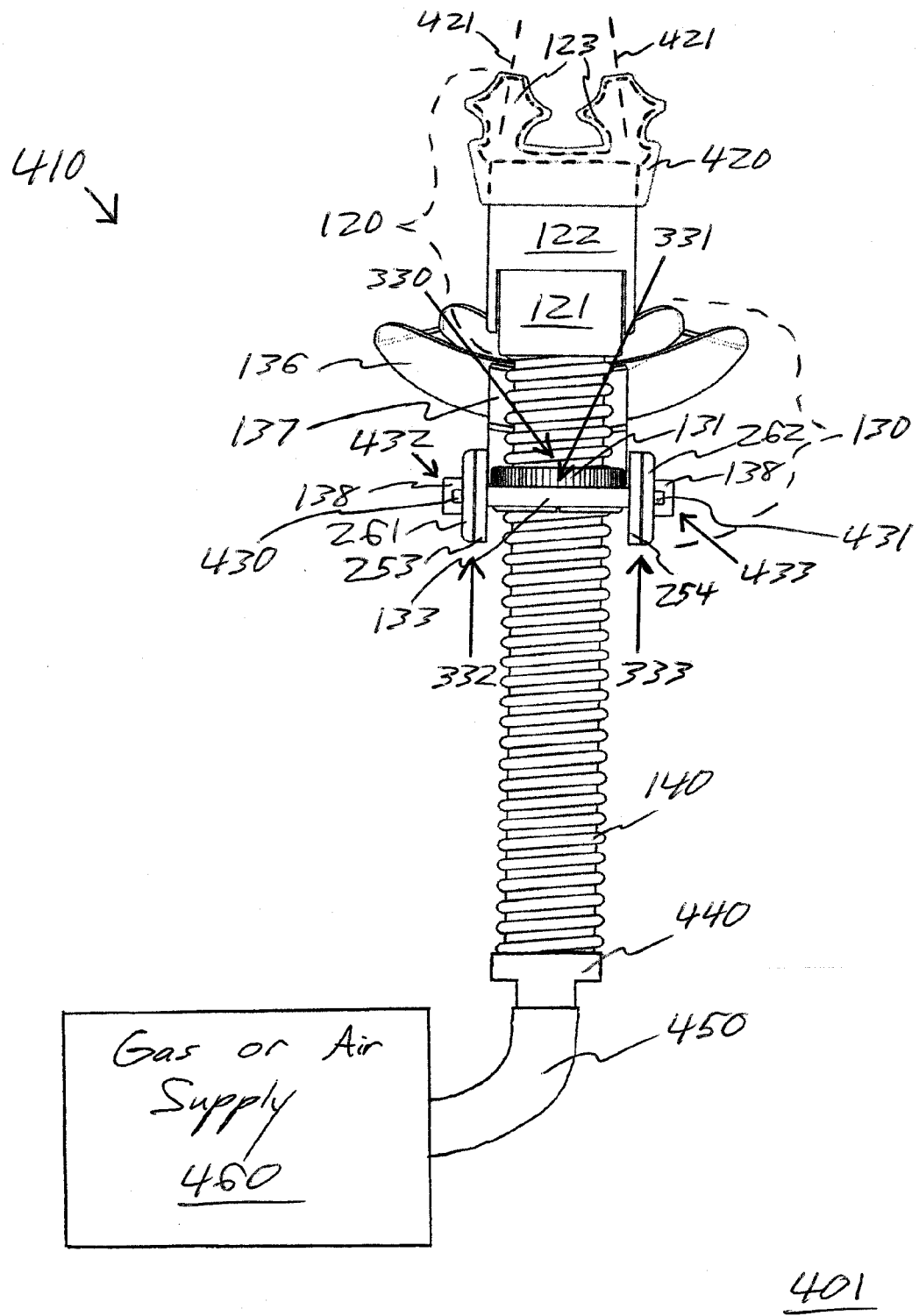
FIG. 4B is a front view of a second exemplary respiratory device in accordance with an embodiment.

With reference now to FIGS. 4A and 4B, side and front views 400, 401, respectively, of a second exemplary respiratory device 410 in accordance with an embodiment is shown. It is noted that second exemplary respiratory device 410 may be substantially similar to first exemplary respiratory device 110 (see discussion above with reference to FIGS. 1-3). It is further noted, however, that second exemplary respiratory device 410 may include a number of components and/or arrangements discussed above with respect to first exemplary respiratory device 110 while also being somewhat different than first exemplary respiratory device 110.

With reference now to the illustrated embodiment, second exemplary respiratory device 410 is shown as including a nasal device 120 coupled with a conveyor device 140. Nasal device 120 includes primary support member 121, which is coupled with or connected to an end of conveyor device 140, as well as a secondary support member 122, which is coupled with or connected to primary support member 121, wherein one or more nasal air intake members 123 are coupled with or extend from secondary support member 122. Moreover, an embodiment provides that primary and secondary support members 121, 122 are capable of rotating relative to one another.

Figure 5:
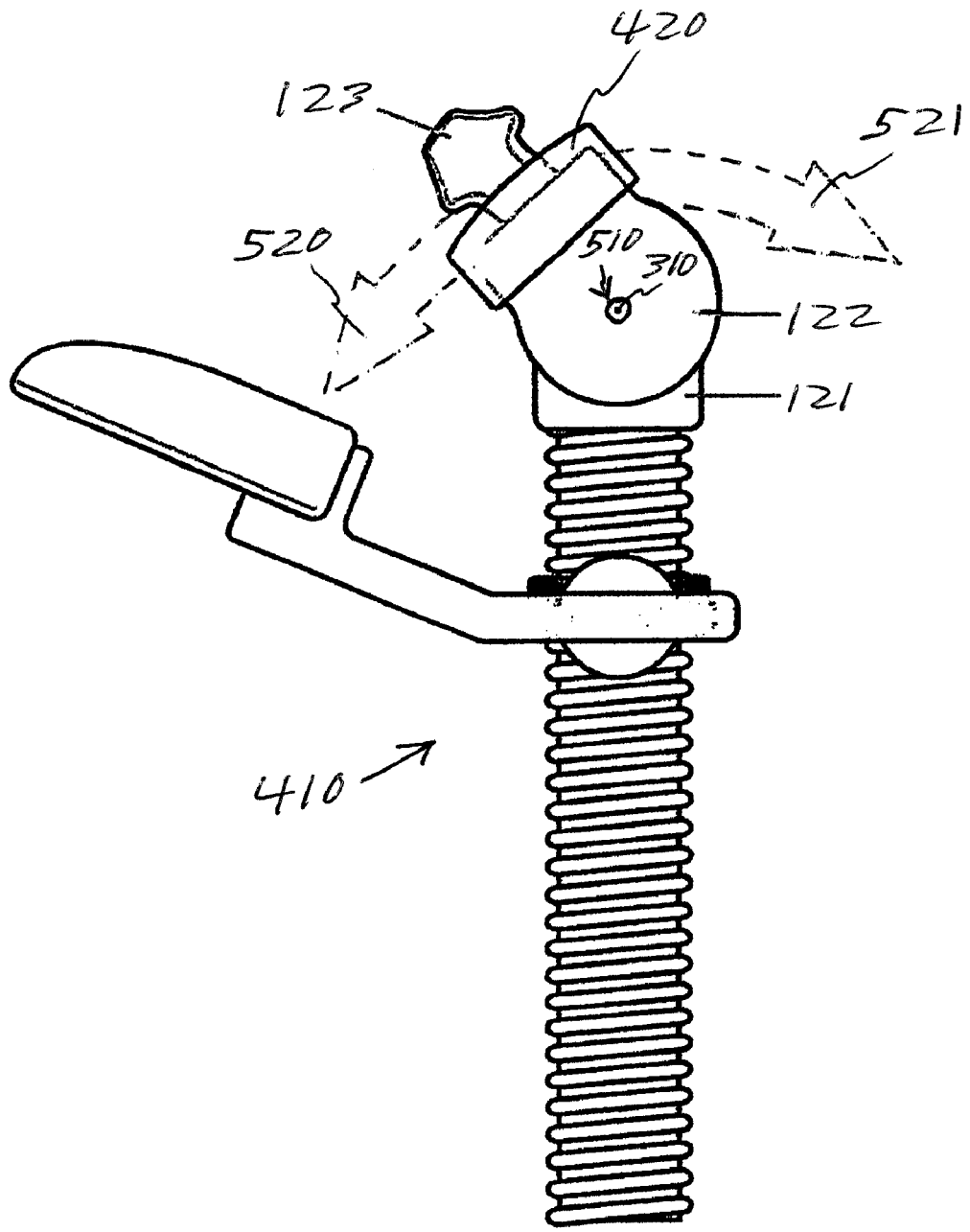
FIG. 5 is a diagram of a first exemplary adjustment configuration in accordance with an embodiment.

To illustrate, and with reference now to FIG. 5, a first exemplary adjustment configuration 500 in accordance with an embodiment is shown. In particular, second exemplary respiratory device 410 is shown as including secondary support member 122, which is moveably coupled with or connected to primary support member 121 about one or more revolute joints, such as revolute joint 510. First exemplary adjustment configuration 500 involves the rotation of secondary support member 122 relative to primary support member 121, or vice versa, about revolute joint 510 and third axis of rotation 310 in first and/or second directions of rotation 520, 521.

With reference again to FIGS. 4A and 4B, it is noted that nasal device 120 may optionally include a cover 420. For example, cover 420 may be a removable cover configured to increase a degree of sanitation associated with second exemplary respiratory device 410. In particular, cover 420 may be periodically removed from nasal device 120 and then cleaned. Cover 420 may then be reattached to nasal device 120 for further use. Indeed, an embodiment provides that cover 420 is fabricated from a flexible material (e.g. rubber) that is sized to conform to a shape of one or more components of nasal device 120. Moreover, a number of holes are defined within each of nasal air intake members 123 and cover 420 along a number of air paths 421 such that gas or air is able to escape from nasal device 120, and travel into a user's nose, when cover 420 is coupled with or attached to nasal air intake members 123.

Furthermore, in accordance with one embodiment, a coupling member 440 is coupled with or attached to an end of conveyor device 140. Additionally, one end of a hose 450 is coupled with or attached to coupling member 440 such that conveyor device 140 is coupled with hose 450, and the other end of hose 450 is coupled with or attached to a gas or air supply 460. Gas or air supply 460 is configured to pump gas or air into hose 450, which then directs this gas or air through coupling member 440 and into conveyor device 140. Conveyor device 140 then directs this gas or air into nasal device 120, which may then be used to direct the gas or air into a user's nostrils.

With reference still to FIGS. 4A and 4B, in an embodiment, second exemplary respiratory device 410 includes oral device 130, which may be configured, for example, to anchor second exemplary respiratory device 410 relative to a user's face during an operation of second exemplary respiratory device 410. It is noted that oral device may include, for example, one or a combination of: adjustment nut 131, first support member 133, second support member 134, dental anchor 136, primary extension 137, and first and second secondary extensions 138, wherein primary extension 137 and first and second secondary extensions 138 may be collectively shaped and/or coupled together to form a fork-shaped extension configuration. Moreover, a number of these components may respectively interact as described above with respect to first exemplary respiratory device 110.

Figure 6:
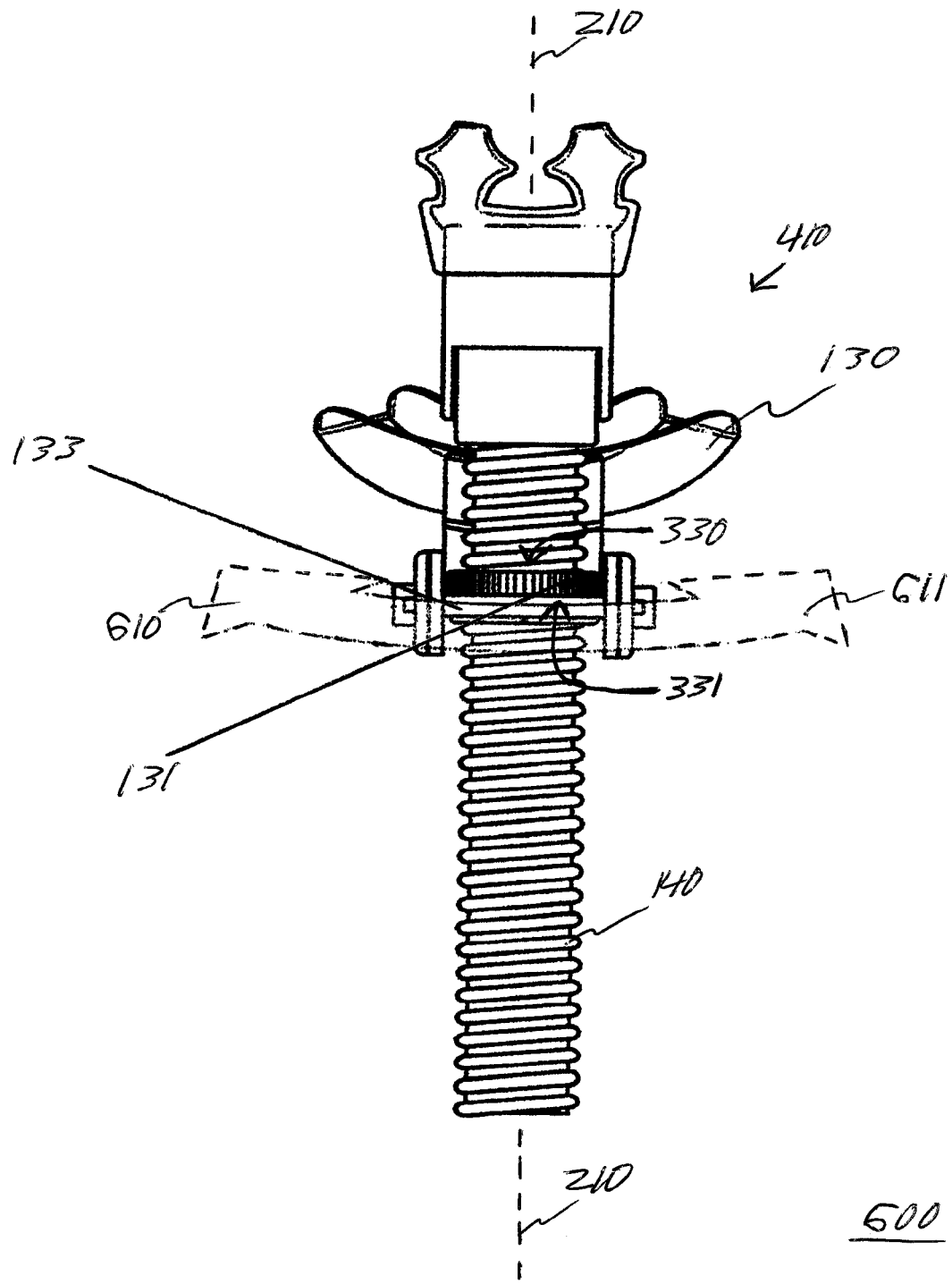
FIG. 6 is a diagram of a second exemplary adjustment configuration in accordance with an embodiment.

In accordance with one embodiment, oral device 130 is moveably coupled with or mounted on conveyor device 140 such that oral device 130 is able to rotate around conveyor device 140, such as about screw joint 330, so as to be repositioned toward one end of conveyor device 140 and away from the other end of conveyor device 140. To illustrate, and with reference now to FIG. 6, a second exemplary adjustment configuration 600 in accordance with an embodiment is shown. In particular, oral device 130 includes adjustment nut 131, which is moveably coupled with or connected to conveyor device 140 about screw joint 330. As such, an embodiment provides that second exemplary adjustment configuration 600 involves the rotation of adjustment nut 131 relative to conveyor device 140, or vice versa, about screw joint 330 and around first axis of rotation 210 such that a distance between nasal device 120 and adjustment nut 131 is either increased or decreased, depending upon the direction of rotation. In this manner, adjustment nut 131 may be rotated, for example, 360 degrees around conveyor device 140 to thereby adjust a height of nasal device 120 relative to oral device 130 based on the threads defined on the inner surface of adjustment nut 131 and the outer surface of conveyor device 140.

Moreover, pursuant to one embodiment, oral device 130 includes both adjustment nut 131 and first support member 133, wherein adjustment nut 131 and first support member 133 are moveably coupled with one another about first revolute joint 331 such that adjustment nut 131 and first support member 133 are able to rotate relative to one another. As such, an embodiment provides that second exemplary adjustment configuration 600 involves the rotation of first support member 133 relative to adjustment nut 131, or vice versa, about first revolute joint 331 and around first axis of rotation 210 in third and/or fourth directions of rotation 610, 611. Indeed, in accordance with one embodiment, second exemplary respiratory device 410 includes both screw joint 330 and first revolute joint 331 such that a plurality of physical joints or degrees of freedom are provided or defined between first support member 133 and conveyor device 140.

With reference again to FIGS. 4A and 4B, an embodiment provides that oral device 130 includes both first and second support members 133, 134, wherein first support member 133 includes first and second coupling members 253, 254, and second support member 134 includes third and fourth coupling members 261, 262. First and third coupling members 253, 261 are moveably coupled with one another about second revolute joint 332 such that first and third coupling members 253, 261 are able to rotate relative to one another. Additionally, second and fourth coupling members 254, 262 are moveably coupled with one another about third revolute joint 333 such that second and fourth coupling members 254, 262 are able to rotate relative to one another.

Figure 7:
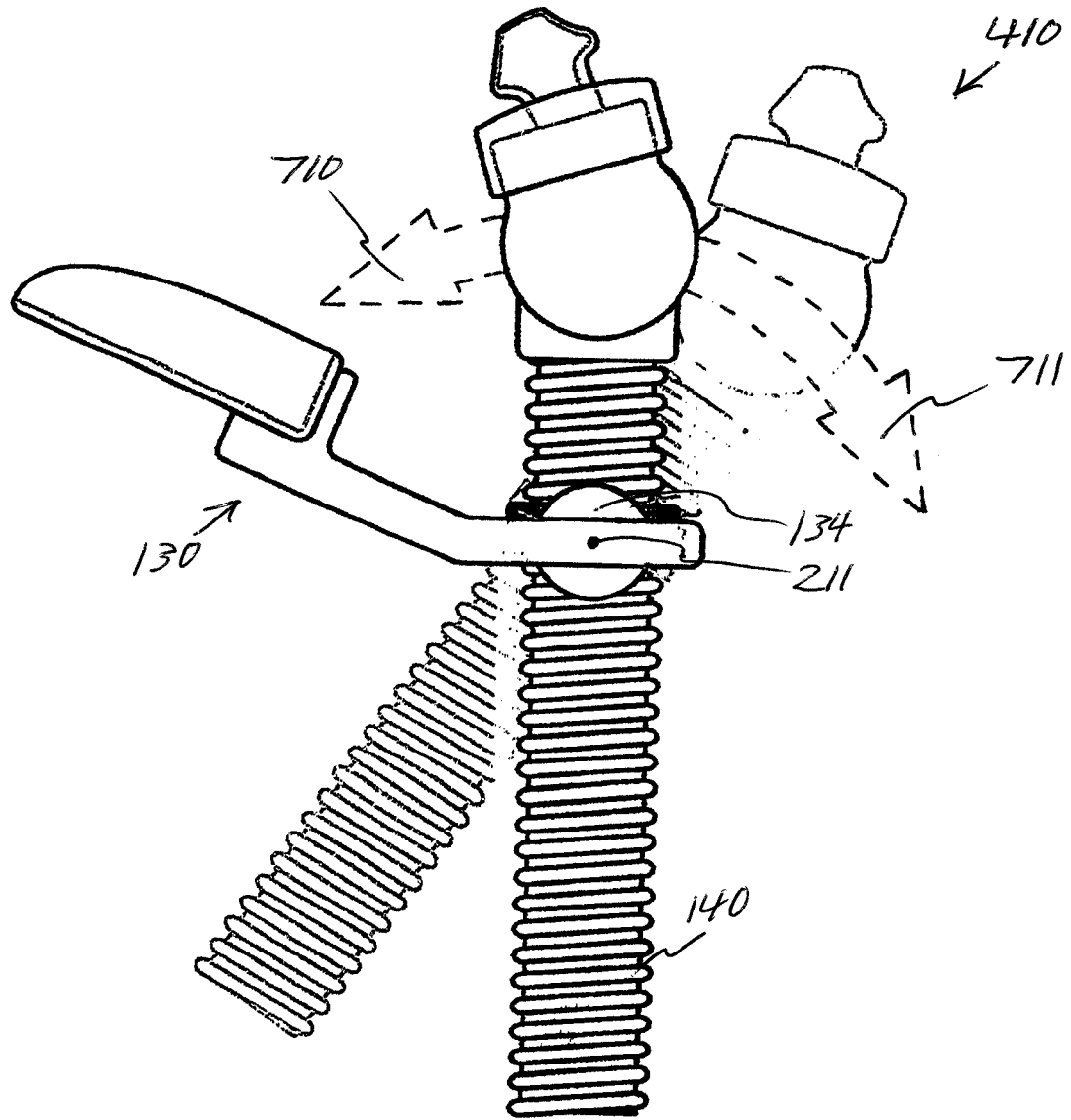
FIG. 7 is a diagram of a third exemplary adjustment configuration in accordance with an embodiment.

To illustrate, and with reference now to FIG. 7, a third exemplary adjustment configuration 700 in accordance with an embodiment is shown. In particular, second exemplary respiratory device 410 is shown as including oral device 130 and conveyor device 140, and third exemplary adjustment configuration 700 involves the rotation of conveyor device 140 relative to oral device 130, or vice versa, around second axis of rotation 211 in fifth and/or sixth directions of rotation 710, 711. Consider the example where oral device 130 includes first support member 133 (as shown in FIG. 4B) and second support member 134, wherein first support member 133 is moveably coupled with or connected to oral device 130 about second and third revolute joints 332, 333 (see FIG. 4B). Third exemplary adjustment configuration 700 involves the rotation of first support member 133 relative to second support member 134, or vice versa, around second axis of rotation 211 in fifth and/or sixth directions of rotation 710, 711.

With reference still to FIG. 4B, in an embodiment, first and second extensions 430, 431 extend from third and fourth coupling members 261, 262, respectively. First and second extensions 430, 431 are sized to fit within receptacles formed within first and second secondary extensions 138, respectively, thereby creating first and second sliding joints 432, 433, respectively, such that first and second secondary extensions 138 are able to slide relative to second support member 134 along first and second linear axes.

Figure 8:
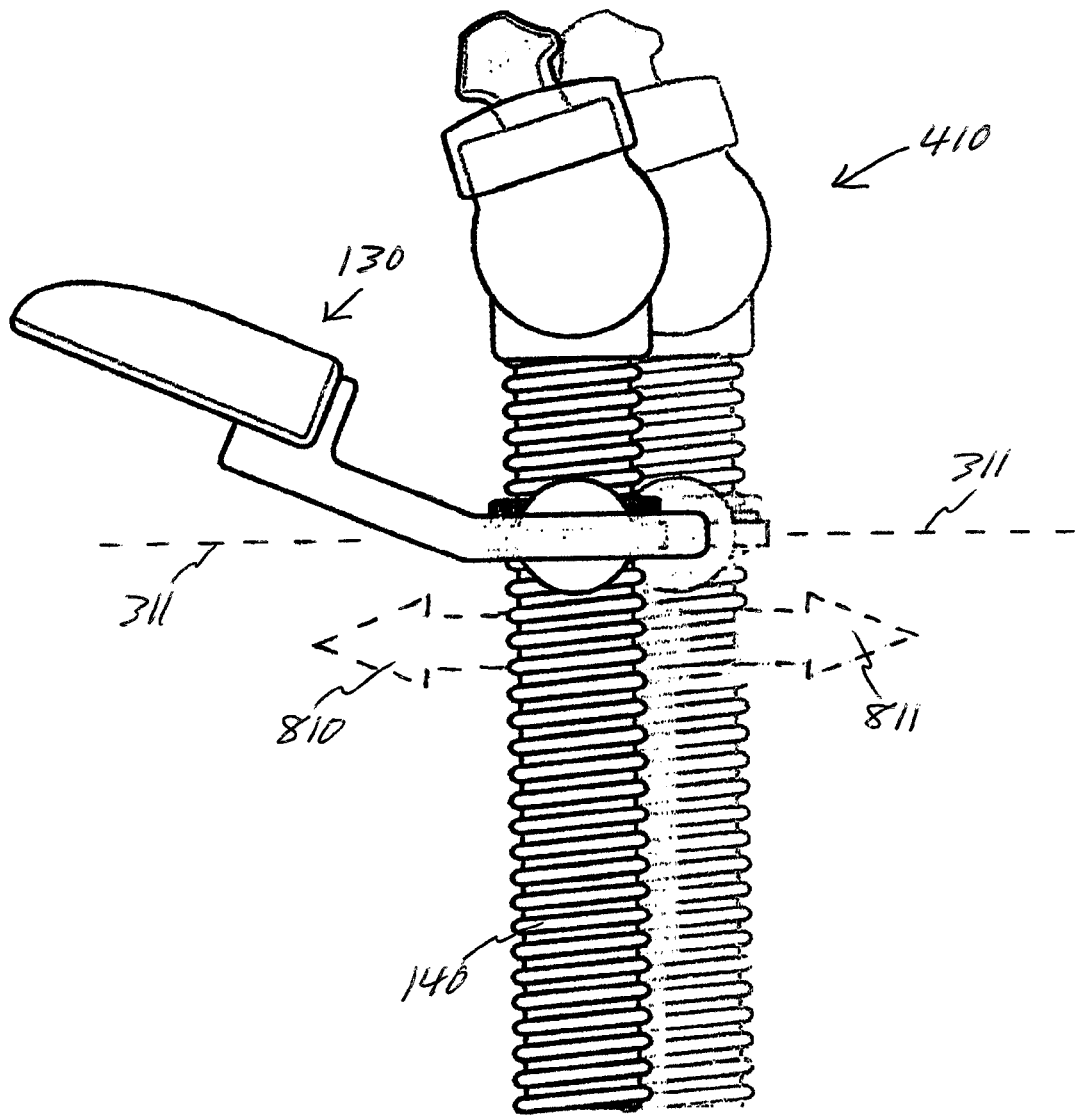
FIG. 8 is a diagram of a fourth exemplary adjustment configuration in accordance with an embodiment.

To illustrate, and with reference now to FIG. 8, a fourth exemplary adjustment configuration 800 in accordance with an embodiment is shown. In particular, second exemplary respiratory device 410 is shown as including conveyor device 140, which is moveably coupled with or connected to oral device 130 about first and second sliding joints 432, 433 (see FIG. 4B). Fourth exemplary adjustment configuration 800 involves the linear movement of conveyor device 140 relative to oral device 130, or vice versa, about first and second sliding joints 432, 433 and along one or more linear axes 311 in first and/or second directions of linear movement 810, 811.

The foregoing notwithstanding, although a number of exemplary joints and mechanical degrees of freedom are described herein, it is noted that one or more of these exemplary joints and mechanical degrees of freedom are optional. Indeed, one or more devices, apparatuses or components described herein may be fixedly coupled together, or combined into a single device, apparatus or component, so as to preclude a presence of one or more of these exemplary joints and mechanical degrees of freedom. Moreover, it is noted that these exemplary joints and mechanical degrees of freedom are presented herein pursuant to a number of exemplary embodiments, and that the present technology is not limited to these exemplary joints and mechanical degrees of freedom. Indeed, one or more other joints and mechanical degrees of freedom may also be implemented.

Summary Concepts

It is noted that the foregoing discussion has presented at least the following concepts:

Concept 1. A respiratory device including or comprising:
   a nasal device;
   a conveyor device coupled or associated with the nasal device; and
   an oral device including or comprising an adjustment nut sized to couple with the conveyor device.

Concept 2. The respiratory device of Concept 1, wherein the adjustment nut is capable of rotating around a first axis of rotation and relative to the conveyor device, the oral device further including or comprising:
   an oral assembly moveably coupled or associated with the adjustment nut such that the oral assembly is capable of rotating around the first axis of rotation and relative to the adjustment nut, the oral assembly including or comprising:
     a first support member moveably coupled or associated with the adjustment nut such that the first support member is capable of rotating around the first axis of rotation and relative to the adjustment nut;
     a second support member moveably coupled or associated with the first support member such that the second support member is capable of rotating around a second axis of rotation and relative to the first support member; and
     an oral member moveably coupled or associated with the second support member such that the oral member is capable of linearly sliding along a number of linear axes and relative to the second support member.

Concept 3. The respiratory device of Concept 1, wherein the nasal device includes or comprises:
   a primary support member coupled or associated with the conveyor device, the conveyor device including or comprising a hose positioned to convey a substance into the primary support member; and
   a secondary support member moveably coupled or associated with the primary support member so as to be rotatable around an axis of rotation and relative to the primary support member, the secondary support member including or comprising one or more nasal air intake members.

Concept 4. A respiratory device including or comprising:
   a nasal device;
   a conveyor device coupled or associated with the nasal device and including or comprising a first surface that defines a first spiral thread; and
   an oral device coupled or associated with the conveyor device and including or comprising an adjustment nut, the adjustment nut including or comprising a second surface that defines a second spiral thread sized to engage the first spiral thread.

Concept 5. The respiratory device of Concept 4, wherein first and second openings are respectively defined at opposite ends of the conveyor device, the adjustment nut sized to rotate around the conveyor device so as to reposition the oral device toward one of the first and second openings and away from the other of the first and second openings.

Concept 6. The respiratory device of Concept 4, wherein the adjustment nut is sized to rotate relative to the conveyor device about a screw joint and around a first axis of rotation, the oral device further including or comprising:

an oral assembly moveably coupled or associated with the adjustment nut, the oral assembly sized to rotate relative to the adjustment nut about a first revolute joint and around the first axis of rotation.

Concept 7. The respiratory device of Concept 6, wherein the oral assembly includes or comprises:

a first support member moveably coupled or associated with the adjustment nut, the adjustment nut sized to rotate relative to the first support member about the first revolute joint and around the first axis of rotation;

a second support member moveably coupled or associated with the first support member, the second support member sized to rotate relative to the first support member about second and third revolute joints and around the second axis of rotation; and an oral member including or comprising:
a dental anchor;
a primary extension extending from the dental anchor; and
first and second secondary extensions extending from the primary extension, the first and second secondary extensions moveably coupled or associated with the second support member and sized to linearly slide relative to the second support member along first and second sliding joints, respectively, and along a number of linear axes.

Concept 8. The respiratory device of Concept 7, wherein the adjustment nut includes or comprises:

a first base member; and
a physical lip extending from the first base member such that a receptacle is defined between the first base member and the physical lip, and
wherein the first support member includes or comprises:
a second base member; and
a protrusion extending from the second base member and sized to engage the receptacle such that the physical lip is capable of supporting the first support member relative to the adjustment nut.

Concept 9. The respiratory device of Concept 8, wherein the first support member further includes or comprises:

first and second coupling members extending from the second base member and including or comprising first and second sets of physical teeth, respectively, and
wherein the second support member includes or comprises:
a third base member; and
third and fourth coupling members extending from the third base member and including or comprising third and fourth sets of physical teeth, respectively, the first and third sets of physical teeth each being sized to engage one another in a first relative tooth arrangement, and the second and fourth sets of physical teeth each being sized to engage one another in a second relative tooth arrangement, such that the first and second support members are capable of supporting one another when in a first relative position associated with the first and second relative tooth arrangements, a rotation of the first coupling member relative to the third coupling member, and of the second coupling member relative to the fourth coupling member, around the second axis of rotation causing the first and third sets of physical teeth to engage one another in a third relative tooth arrangement, and the second and fourth sets of physical teeth to engage one another in a fourth relative tooth arrangement, such that the first and second support members are capable of supporting one another when in a second relative position associated with the third and fourth relative tooth arrangements.

Concept 10. The respiratory device of Concept 9, wherein the first and second secondary extensions comprise:

first and second groups of physical teeth, respectively, the third and fourth coupling members further including or comprising third and fourth groups of physical teeth, respectively, the first and third groups of physical teeth each being sized to engage one another in a fifth relative tooth arrangement, and the second and fourth groups of physical teeth each being sized to engage one another in a sixth relative tooth arrangement, such that the first and second secondary extensions are capable of supporting the second support member when the first and second secondary extensions and the second support member are in a third relative position associated with the fifth and sixth relative tooth arrangements, a linear movement of the first secondary extension relative to the third coupling member along the first sliding joint, and of the second secondary extension relative to the fourth coupling member along the second sliding joint, causing the first and third groups of physical teeth to engage one another in a seventh relative tooth arrangement, and the second and fourth groups of physical teeth to engage one another in an eighth relative tooth arrangement, such that the first and second secondary extensions are capable of supporting the second support member when the first and second secondary extensions and the second support member are in a fourth relative position associated with the seventh and eighth relative tooth arrangements.

Concept 11. The respiratory device of Concept 4, wherein the nasal device includes or comprises:

a primary support member coupled or associated with the conveyor device, the conveyor device including or comprising a hose positioned to convey a substance into the primary support member; and a secondary support member moveably coupled or associated with the primary support member about primary and secondary revolute joints so as to be rotatable around an axis of rotation and relative to the primary support member, the secondary support member including or comprising one or more nasal air intake members.

Concept 12. The respiratory device of Concept 11, wherein one support member from among the primary and secondary support members includes or comprises first and second protrusions positioned along the axis of rotation, and the other support member from among the primary and secondary support members including or comprising first and second receptacles defined therein along the axis of rotation, the first and second receptacles sized to receive the first and second protrusions such that the primary and secondary support members are capable of supporting one another, and such that the primary and secondary support members are capable of rotating relative to one another about the axis of rotation.

Concept 13. A respiratory device including or comprising:
a nasal device;
a conveyor device coupled or associated with the nasal device, first and second openings being respectively defined at opposite ends of the conveyor device; and an oral device coupled or associated with the conveyor device, the oral device sized to rotate around the conveyor device so as to be repositioned toward one of the first and second openings and away from the other of the first and second openings.

Concept 14. The respiratory device of Concept 13, wherein the conveyor device includes or comprises a first surface that defines a first spiral thread, the oral device including or comprising an adjustment nut, and the adjustment nut including or comprising a second surface that defines a second spiral thread sized to engage the first spiral thread.

Concept 15. The respiratory device of Concept 14, wherein the adjustment nut is sized to rotate relative to the conveyor device about a screw joint and around a first axis of rotation, the oral device further including or comprising:

an oral assembly moveably coupled or associated with the adjustment nut, the oral assembly sized to rotate relative to the adjustment nut about a first revolute joint and around the first axis of rotation.

Concept 16. The respiratory device of Concept 15, wherein the oral assembly includes or comprises:

a first support member moveably coupled or associated with the adjustment nut, the adjustment nut sized to rotate relative to the first support member about the first revolute joint and around the first axis of rotation;

a second support member moveably coupled or associated with the first support member, the second support member sized to rotate relative to the first support member about second and third revolute joints and around the second axis of rotation; and an oral member including or comprising:
a dental anchor;
a primary extension extending from the dental anchor; and
first and second secondary extensions extending from the primary extension, the first and second secondary extensions moveably coupled or associated with the second support member and sized to linearly slide relative to the second support member along first and second sliding joints, respectively, and along a number of linear axes.

Concept 17. The respiratory device of Concept 16, wherein the adjustment nut includes or comprises:

a first base member; and
a physical lip extending from the first base member such that a receptacle is defined between the first base member and the physical lip, and wherein the first support member includes or comprises:
a second base member; and
a protrusion extending from the second base member and sized to engage the receptacle such that the physical lip is capable of supporting the first support member relative to the adjustment nut.

Concept 18. The respiratory device of Concept 17, wherein the first support member further includes or comprises:

first and second coupling members extending from the second base member and including or comprising first and second sets of physical teeth, respectively, and wherein the second support member includes or comprises:
a third base member; and
third and fourth coupling members extending from the third base member and including or comprising third and fourth sets of physical teeth, respectively, the first and third sets of physical teeth each being sized to engage one another in a first relative tooth arrangement, and the second and fourth sets of physical teeth each being sized to engage one another in a second relative tooth arrangement, such that the first and second support members are capable of supporting one another when in a first relative position associated with the first and second relative tooth arrangements, a rotation of the first coupling member relative to the third coupling member, and of the second coupling member relative to the fourth coupling member, around the second axis of rotation causing the first and third sets of physical teeth to engage one another in a third relative tooth arrangement, and the second and fourth sets of physical teeth to engage one another in a fourth relative tooth arrangement, such that the first and second support members are capable of supporting one another when in a second relative position associated with the third and fourth relative tooth arrangements.

Concept 19. The respiratory device of Concept 18, wherein the first and second secondary extensions comprise:

first and second groups of physical teeth, respectively, the third and fourth coupling members further including or comprising third and fourth groups of physical teeth, respectively, the first and third groups of physical teeth each being sized to engage one another in a fifth relative tooth arrangement, and the second and fourth groups of physical teeth each being sized to engage one another in a sixth relative tooth arrangement, such that the first and second secondary extensions are capable of supporting the second support member when the first and second secondary extensions and the second support member are in a third relative position associated with the fifth and sixth relative tooth arrangements, a linear movement of the first secondary extension relative to the third coupling member along the first sliding joint, and of the second secondary extension relative to the fourth coupling member along the second sliding joint, causing the first and third groups of physical teeth to engage one another in a seventh relative tooth arrangement, and the second and fourth groups of physical teeth to engage one another in an eighth relative tooth arrangement, such that the first and second secondary extensions are capable of supporting the second support member when the first and second secondary extensions and the second support member are in a fourth relative position associated with the seventh and eighth relative tooth arrangements.

Concept 20. The respiratory device of Concept 13, wherein the nasal device includes or comprises:

a primary support member coupled or associated with the conveyor device, the conveyor device including or comprising a hose positioned to convey a substance into the primary support member; and a secondary support member moveably coupled or associated with the primary support member about primary and secondary revolute joints so as to be rotatable around an axis of rotation and relative to the primary support member, the secondary support member including or comprising one or more nasal air intake members.

Concept 21. An oral device including or comprising:
an adjustment member including or comprising a surface that defines a spiral thread.

Concept 22. The oral device of Concept 21, further including or comprising:

an oral assembly moveably coupled or associated with the adjustment member such that the oral assembly is capable of rotating relative to the adjustment member.

Although various exemplary embodiments of the present technology are described herein in a language specific to structural features and/or methodological acts, the subject matter defined in the appended claims is not necessarily limited to the specific features or acts described above. Rather, the specific features and acts described above are disclosed as exemplary forms of implementing the claims.

What is claimed is:

1. A respiratory device comprising:
 a nasal device;
 a conveyor device coupled with said nasal device; and
 an oral device coupled with said conveyor device and comprising:
  an adjustment nut comprising first and second surfaces, said first surface sized to engage said conveyor device, and
  an oral assembly sized to engage said second surface such that said oral assembly is able to rotate around said adjustment nut, said oral assembly remaining engaged with said second surface, and a distance between said oral assembly and said second surface remaining unchanged, when said adjustment nut rotates, relative to said oral assembly, a full revolution around said conveyor device.

2. The respiratory device of claim 1, wherein said adjustment nut is capable of rotating around a first axis of rotation and relative to said conveyor device, said oral assembly being moveably coupled with said adjustment nut such that said oral assembly is capable of rotating around said first axis of rotation and relative to said adjustment nut, and said oral assembly comprising:
 a first support member moveably coupled with said adjustment nut such that said first support member is capable of rotating around said first axis of rotation and relative to said adjustment nut;
 a second support member moveably coupled with said first support member such that said second support member is capable of rotating around a second axis of rotation and relative to said first support member; and
 an oral member moveably coupled with said second support member such that said oral member is capable of linearly sliding along a number of linear axes and relative to said second support member.

3. The respiratory device of claim 1, wherein said nasal device comprises:
 a primary support member coupled with said conveyor device, said conveyor device comprising a hose positioned to convey a substance into said primary support member; and
 a secondary support member moveably coupled with said primary support member so as to be rotatable around an axis of rotation and relative to said primary support member, said secondary support member comprising one or more nasal air intake members.

4. A respiratory device comprising:
 a nasal device;
 a conveyor device coupled with said nasal device and comprising a first surface that defines a first spiral thread; and
 an oral device coupled with said conveyor device and comprising:
  an adjustment nut comprising second and third surfaces, said second surface defining a second spiral thread sized to engage said first spiral thread, and
  an oral assembly sized to engage said third surface such that said oral assembly is able to rotate around said adjustment nut, said oral assembly remaining engaged with said third surface, and a distance between said oral assembly and said third surface remaining unchanged, when said adjustment nut rotates, relative to said oral assembly, a full revolution around said conveyor device.

5. The respiratory device of claim 4, wherein first and second openings are respectively defined at opposite ends of said conveyor device, said adjustment nut sized to rotate around said conveyor device so as to reposition said oral device toward one of said first and second openings and away from the other of said first and second openings.

6. The respiratory device of claim 4, wherein said adjustment nut is sized to rotate relative to said conveyor device about a screw joint and around a first axis of rotation, said oral assembly being moveably coupled with said adjustment nut, and said oral assembly sized to rotate relative to said adjustment nut about a first revolute joint and around said first axis of rotation.

7. The respiratory device of claim 6, wherein said oral assembly comprises:
 a first support member moveably coupled with said adjustment nut, said adjustment nut sized to rotate relative to said first support member about said first revolute joint and around said first axis of rotation;
 a second support member moveably coupled with said first support member, said second support member sized to rotate relative to said first support member about second and third revolute joints and around a second axis of rotation; and
 an oral member comprising:
 a dental anchor;
 a primary extension extending from said dental anchor; and
 first and second secondary extensions extending from said primary extension, said first and second secondary extensions moveably coupled with said second support member and sized to linearly slide relative to said second support member along first and second sliding joints, respectively, and along a number of linear axes.

8. The respiratory device of claim 7, wherein said adjustment nut comprises:
 a first base member; and
 a physical lip extending from said first base member such that a receptacle is defined between said first base member and said physical lip, and
 wherein said first support member comprises:
 a second base member; and
 a protrusion extending from said second base member and sized to engage said receptacle such that said physical lip is capable of supporting said first support member relative to said adjustment nut.

9. The respiratory device of claim 8, wherein said first support member further comprises:
 first and second coupling members extending from said second base member and comprising first and second sets of physical teeth, respectively, and
 wherein said second support member comprises:
 a third base member; and
 third and fourth coupling members extending from said third base member and comprising third and fourth sets of physical teeth, respectively, said first and third sets of physical teeth each being sized to engage one another in a first relative tooth arrangement, and said second and fourth sets of physical teeth each being sized to engage one another in a second relative tooth arrangement, such that said first and second support members are capable of supporting one another when in a first relative position associated with said first and second relative tooth arrangements, a rotation of said first coupling member relative to said third coupling member, and of said second coupling member relative to said fourth coupling member, around said second axis of rotation causing said first and third sets of physical teeth to engage one another in a third relative tooth arrangement, and said second and fourth sets of physical teeth to engage one another in a fourth relative tooth arrangement, such that said first and second support members are capable of supporting one another when in a second relative position associated with said third and fourth relative tooth arrangements.

10. The respiratory device of claim 9, wherein said first and second secondary extensions comprise:
first and second groups of physical teeth, respectively, said third and fourth coupling members further comprising third and fourth groups of physical teeth, respectively, said first and third groups of physical teeth each being sized to engage one another in a fifth relative tooth arrangement, and said second and fourth groups of physical teeth each being sized to engage one another in a sixth relative tooth arrangement, such that said first and second secondary extensions are capable of supporting said second support member when said first and second secondary extensions and said second support member are in a third relative position associated with said fifth and sixth relative tooth arrangements, a linear movement of said first secondary extension relative to said third coupling member along said first sliding joint, and of said second secondary extension relative to said fourth coupling member along said second sliding joint, causing said first and third groups of physical teeth to engage one another in a seventh relative tooth arrangement, and said second and fourth groups of physical teeth to engage one another in an eighth relative tooth arrangement, such that said first and second secondary extensions are capable of supporting said second support member when said first and second secondary extensions and said second support member are in a fourth relative position associated with said seventh and eighth relative tooth arrangements.

11. The respiratory device of claim 4, wherein said nasal device comprises:
a primary support member coupled with said conveyor device, said conveyor device comprising a hose positioned to convey a substance into said primary support member; and
a secondary support member moveably coupled with said primary support member about primary and secondary revolute joints so as to be rotatable around an axis of rotation and relative to said primary support member, said secondary support member comprising one or more nasal air intake members.

12. The respiratory device of claim 11, wherein one support member from among said primary and secondary support members comprises first and second protrusions positioned along said axis of rotation, and the other support member from among said primary and secondary support members comprising first and second receptacles defined therein along said axis of rotation, said first and second receptacles sized to receive said first and second protrusions such that said primary and secondary support members are capable of supporting one another, and such that said primary and secondary support members are capable of rotating relative to one another about said axis of rotation.

13. A respiratory device comprising:
a nasal device;
a conveyor device coupled with said nasal device, first and second openings being respectively defined at opposite ends of said conveyor device; and
an oral device coupled with said conveyor device, said oral device sized to rotate around said conveyor device so as to be repositioned toward one of said first and second openings and away from the other of said first and second openings, and said oral device comprising:

an adjustment member comprising first and second surfaces, said first surface sized to engage said conveyor device, and
an oral assembly sized to engage said second surface such that said oral assembly is able to rotate around said adjustment member, said oral assembly remaining engaged with said second surface, and a distance between said oral assembly and said second surface remaining unchanged, when said adjustment member rotates, relative to said oral assembly, a full revolution around said conveyor device.

14. The respiratory device of claim 13, wherein said conveyor device comprises a third surface that defines a first spiral thread, said first surface defining a second spiral thread sized to engage said first spiral thread.

15. The respiratory device of claim 14, wherein said adjustment nut is sized to rotate relative to said conveyor device about a screw joint and around a first axis of rotation, said oral assembly being moveably coupled with said adjustment nut, and said oral assembly sized to rotate relative to said adjustment nut about a first revolute joint and around said first axis of rotation.

16. The respiratory device of claim 15, wherein said oral assembly comprises:
a first support member moveably coupled with said adjustment nut, said adjustment nut sized to rotate relative to said first support member about said first revolute joint and around said first axis of rotation;
a second support member moveably coupled with said first support member, said second support member sized to rotate relative to said first support member about second and third revolute joints and around a second axis of rotation; and
an oral member comprising:
a dental anchor;
a primary extension extending from said dental anchor; and
first and second secondary extensions extending from said primary extension, said first and second secondary extensions moveably coupled with said second support member and sized to linearly slide relative to said second support member along first and second sliding joints, respectively, and along a number of linear axes.

17. The respiratory device of claim 16, wherein said adjustment nut comprises:
a first base member; and
a physical lip extending from said first base member such that a receptacle is defined between said first base member and said physical lip, and
wherein said first support member comprises:
a second base member; and
a protrusion extending from said second base member and sized to engage said receptacle such that said physical lip is capable of supporting said first support member relative to said adjustment nut.

18. The respiratory device of claim 17, wherein said first support member further comprises:
first and second coupling members extending from said second base member and comprising first and second sets of physical teeth, respectively, and
wherein said second support member comprises:
a third base member; and
third and fourth coupling members extending from said third base member and comprising third and fourth sets of physical teeth, respectively, said first and third sets of physical teeth each being sized to engage one another in a first relative tooth arrangement, and said second and fourth sets of physical teeth each being sized to engage one another in a second relative tooth arrangement, such that said first and second support members are capable of supporting one another when in a first relative position associated with said first and second relative tooth arrangements, a rotation of said first coupling member relative to said third coupling member, and of said second coupling member relative to said fourth coupling member, around said second axis of rotation causing said first and third sets of physical teeth to engage one another in a third relative tooth arrangement, and said second and fourth sets of physical teeth to engage one another in a fourth relative tooth arrangement, such that said first and second support members are capable of supporting one another when in a second relative position associated with said third and fourth relative tooth arrangements.

19. The respiratory device of claim 18, wherein said first and second secondary extensions comprise:
first and second groups of physical teeth, respectively, said third and fourth coupling members further comprising third and fourth groups of physical teeth, respectively, said first and third groups of physical teeth each being sized to engage one another in a fifth relative tooth arrangement, and said second and fourth groups of physical teeth each being sized to engage one another in a sixth relative tooth arrangement, such that said first and second secondary extensions are capable of supporting said second support member when said first and second secondary extensions and said second support member are in a third relative position associated with said fifth and sixth relative tooth arrangements, a linear movement of said first secondary extension relative to said third coupling member along said first sliding joint, and of said second secondary extension relative to said fourth coupling member along said second sliding joint, causing said first and third groups of physical teeth to engage one another in a seventh relative tooth arrangement, and said second and fourth groups of physical teeth to engage one another in an eighth relative tooth arrangement, such that said first and second secondary extensions are capable of supporting said second support member when said first and second secondary extensions and said second support member are in a fourth relative position associated with said seventh and eighth relative tooth arrangements.

20. The respiratory device of claim 13, wherein said nasal device comprises:
a primary support member coupled with said conveyor device, said conveyor device comprising a hose positioned to convey a substance into said primary support member; and
a secondary support member moveably coupled with said primary support member about primary and secondary revolute joints so as to be rotatable around an axis of rotation and relative to said primary support member, said secondary support member comprising one or more nasal air intake members.

* * * * *